US012564371B2

(12) United States Patent
Sohlden et al.

(10) Patent No.: US 12,564,371 B2
(45) Date of Patent: Mar. 3, 2026

(54) SYSTEM AND METHOD FOR DISPLAYING ABLATION ZONE PROGRESSION

(71) Applicant: Covidien LP, Mansfield, MA (US)

(72) Inventors: Ryan S. Sohlden, Lyons, CO (US); Kaylen J. Haley, North Kingstown, RI (US); Casey M. Ladtkow, Erie, CO (US)

(73) Assignee: Covidien LP, Mansfield, MA (US)

( * ) Notice: Subject to any disclaimer, the term of this patent is extended or adjusted under 35 U.S.C. 154(b) by 59 days.

(21) Appl. No.: 18/459,596

(22) Filed: Sep. 1, 2023

(65) Prior Publication Data

US 2024/0090866 A1      Mar. 21, 2024

Related U.S. Application Data

(60) Provisional application No. 63/407,762, filed on Sep. 19, 2022.

(51) Int. Cl.
*A61B 8/08*        (2006.01)
*A61B 8/00*        (2006.01)
*A61B 18/18*       (2006.01)

(52) U.S. Cl.
CPC ............ *A61B 8/0841* (2013.01); *A61B 8/463* (2013.01); *A61B 8/481* (2013.01); *A61B 18/1815* (2013.01)

(58) Field of Classification Search
None
See application file for complete search history.

(56) References Cited

U.S. PATENT DOCUMENTS

| | | | |
|---|---|---|---|
| 11,013,557 B2 | 5/2021 | van der Weide et al. | |
| 11,284,813 B2 | 3/2022 | Shmayahu et al. | |
| 2012/0189998 A1 | 7/2012 | Kruecker et al. | |
| 2012/0237105 A1 | 9/2012 | Mielekamp | |
| 2014/0201669 A1* | 7/2014 | Liu ........................ | A61B 34/10 |
| | | | 715/771 |
| 2016/0317224 A1 | 11/2016 | Girotto et al. | |
| 2016/0374646 A1 | 12/2016 | Case et al. | |
| 2019/0133696 A1 | 5/2019 | Spero | |
| 2019/0151026 A1 | 5/2019 | Lu et al. | |
| 2020/0046435 A1 | 2/2020 | Ladtkow et al. | |
| 2022/0287767 A1* | 9/2022 | Xu ..................... | A61B 18/1492 |
| 2023/0157757 A1* | 5/2023 | Braido ................. | G06T 19/003 |
| | | | 345/419 |

FOREIGN PATENT DOCUMENTS

WO    WO-2020131506 A1 *   6/2020   ......... A61B 18/1815

* cited by examiner

*Primary Examiner* — Patricia J Park
(74) *Attorney, Agent, or Firm* — Carter, DeLuca & Farrel

(57) ABSTRACT

An ablation system includes an ablation device configured to ablate a target, an imaging device, and a computing device. The imaging device is configured to capture images of a surgical site, in real time, including the target and the ablation device positioned relative to the target. The computing device includes a display configured to display a user interface. The user interface includes the images of the surgical site in real time and a simulation of ablation growth overlayed onto the images of the surgical site. Dimensions of the simulation of ablation growth may be based on expected ablation zone sizes for a fixed power setting at different energy application durations.

20 Claims, 5 Drawing Sheets

400

403

405

318

SYSTEM AND METHOD FOR DISPLAYING ABLATION ZONE PROGRESSION

CROSS-REFERENCE TO RELATED APPLICATION

This application claims the benefit of the filing date of provisional U.S. Patent Application No. 63/407,762, filed on Sep. 19, 2022.

FIELD

The present disclosure relates to systems, methods, and devices for displaying ablation zone progression during a microwave ablation treatment procedure.

BACKGROUND

When planning a treatment procedure, clinicians often rely on patient data including X-ray data, computed tomography (CT) scan data, magnetic resonance imaging (MRI) data, or other imaging data that allows the clinician to view the internal anatomy of a patient. The clinician utilizes the patient data to identify targets of interest and to develop strategies for accessing the targets of interest for the treatment procedure.

Existing imaging modalities introduce unique challenges when monitoring the progression of an ablation zone during an ablation procedure. Ultrasound imaging displays "bubbles" or ground glass opacity as energy is delivered, making it difficult to determine the edge of the actual ablation zone during progression of the application of energy. CT imaging provides "near-time" imaging that reflects the ablation zone size at the time that the last scan was captured, however, does not reflect ablation growth as it occurs in real time.

SUMMARY

Systems and methods for displaying ablation zone progression during a microwave ablation treatment procedure are provided.

According to an aspect of the present disclosure, an ablation system includes an ablation device configured to ablate a target, an imaging device, and a computing device. The imaging device is configured to capture images of a surgical site in real time. The images of the surgical site include the target and the ablation device positioned relative to the target. The computing device includes a display configured to display a user interface. The user interface includes the images of the surgical site in real time and a simulation of ablation growth overlayed onto the images of the surgical site. Dimensions of the simulation of ablation growth may be based on expected ablation zone sizes for a given power setting at different energy application durations.

In an aspect, the imaging device is an ultrasound imaging device, and the images of the surgical site are ultrasound images.

In an aspect, the simulation of ablation growth includes a solid outer edge.

In an aspect, the simulation of ablation growth includes a jagged line outer edge.

In an aspect, the simulation of ablation growth includes a pulsing line outer edge which fades between appearing and disappearing.

In an aspect, the expected ablation zone sizes are based on previously acquired data samples.

In an aspect, the expected ablation zone sizes are based on MRI telemetry data.

In an aspect, the expected ablation zone sizes are based on inferences from contrast enhanced ultrasound.

In accordance with another aspect of the disclosure, an ablation system includes a computing device including a display. The computing device is configured to receive images of a surgical site in real time, which include a target and an ablation device positioned relative to the target, display the received images on the display, and overlay a simulation of ablation growth onto the displayed images of the surgical site. Dimensions of the simulation of ablation growth may be based on expected ablation zone sizes at different energy application durations.

In an aspect, the system may further include an ultrasound imaging device.

In an aspect, the simulation of ablation growth includes a solid outer edge.

In an aspect, the simulation of ablation growth includes a jagged line outer edge.

In an aspect, the simulation of ablation growth includes a pulsing line outer edge which fades between appearing and disappearing.

In an aspect, the expected ablation zone sizes are based on previously acquired data samples.

In an aspect, the expected ablation zone sizes are based on MRI telemetry data.

In an aspect, the expected ablation zone sizes are based on inferences from contrast enhanced ultrasound.

In accordance with another aspect of the disclosure, a user interface is provided. The user interface includes real time images of a surgical site and a simulation of ablation growth overlayed onto the real time images of the surgical site. The real time images of the surgical site include a target and an ablation device positioned relative to the target. The dimensions of the simulation of ablation growth may be based on expected ablation zone sizes at different energy application durations.

In an aspect, the simulation of ablation growth includes at least one of a solid outer edge, a jagged line outer edge, or a pulsing line outer edge which fades between appearing and disappearing.

In an aspect, the expected ablation zone sizes are based on previously acquired data samples.

In an aspect, the expected ablation zone sizes are based on at least one of MRI telemetry data or inferences from contrast enhanced ultrasound.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which.

DETAILED DESCRIPTION

The present disclosure provides a system and method for displaying ablation zone progression during a microwave ablation treatment procedure.

Although the present disclosure will be described in terms of specific illustrative embodiments, it will be readily apparent to those skilled in the art that various modifications, rearrangements, and substitutions may be made without departing from the spirit of the present disclosure. The scope of the present disclosure is defined by the claims appended hereto.

Figure 1:
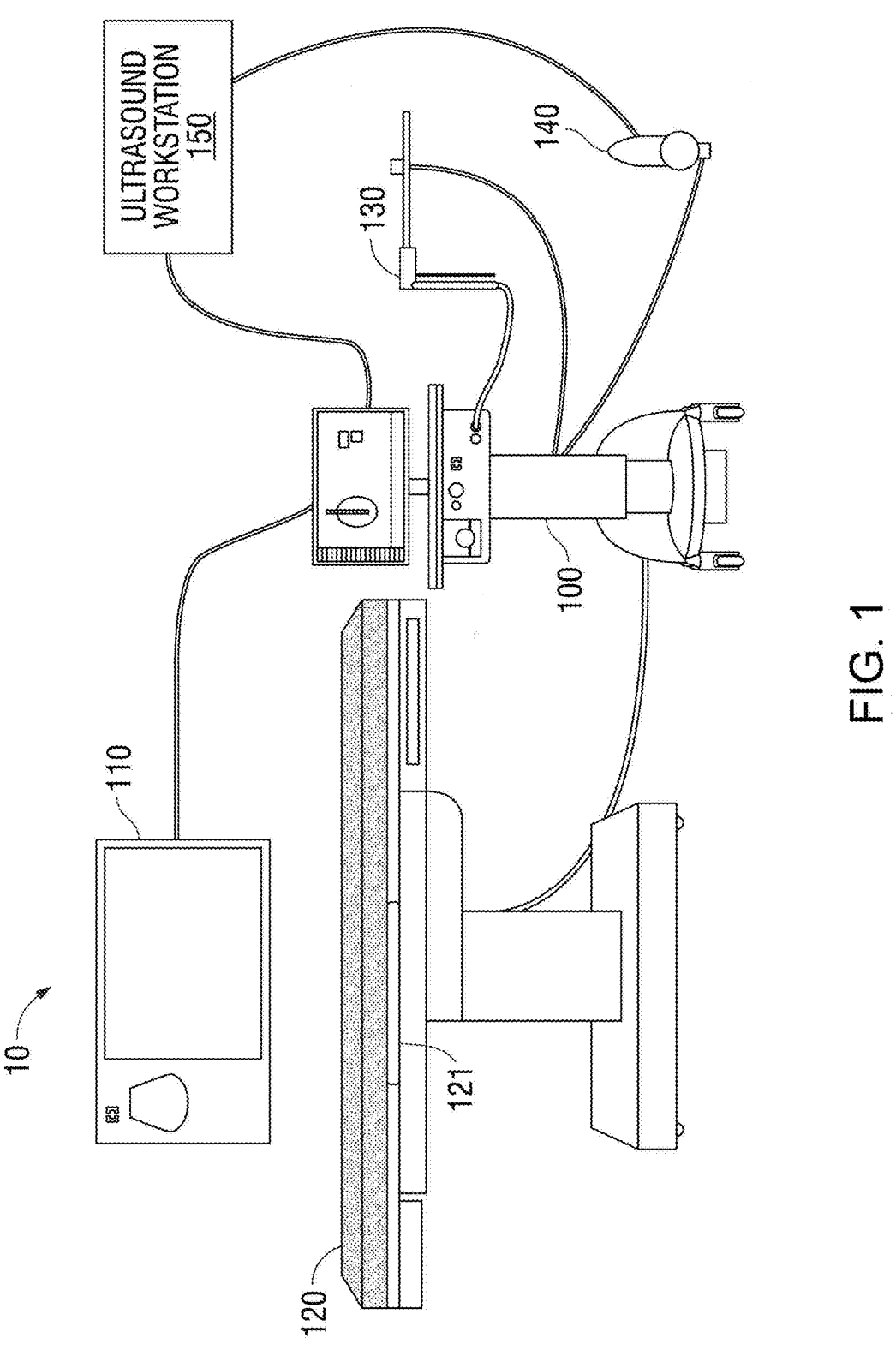
FIG. 1 is a schematic diagram of a microwave ablation procedure system in accordance with an illustrative aspect of the present disclosure.

Referring to FIG. 1, a treatment system 10 includes a computing device 100, a display 110, a table 120, an ablation device 130, and an ultrasound imaging device 140 connected to an ultrasound workstation 150. Computing device 100 may be, for example, a laptop computer, desktop computer, tablet computer, or other similar device. Computing device 100 may be configured to control an electrosurgical generator, a peristaltic pump, a power supply, and/or any other accessories and peripheral devices relating to, or forming part of, system 10. Display 110 is configured to output instructions, images, and messages relating to the performance of the microwave ablation procedure. Table 120 may be, for example, an operating table or other table suitable for use during a surgical procedure, which includes an electromagnetic (EM) field generator 121. EM field generator 121 is used to generate an EM field during the microwave ablation procedure and forms part of an EM tracking system that is used to track the positions of surgical instruments within the body of a patient. EM field generator 121 may include various components, such as a specially designed pad to be placed under, or integrated into, an operating table or patient bed. An example of such an EM tracking system is the AURORA™ tracking system sold by Northern Digital Inc. Ablation device 130 is a surgical instrument having a microwave ablation antenna that is used to ablate tissue. While the present disclosure describes the use of system 10 in a surgical environment, it is also envisioned that some or all of the components of system 10 may be used in alternative settings, for example, an imaging laboratory and/or an office setting.

In addition to the EM tracking system, the surgical instruments may also be visualized by using ultrasound imaging. Ultrasound imaging device 140, such as an ultrasound wand, may be used to image the patient's body during the microwave ablation procedure to visualize the location of the surgical instruments, such as ablation device 130, inside the patient's body. Ultrasound imaging device 140 may have an EM tracking sensor embedded within or attached to the ultrasound wand, for example, a clip-on sensor or a sticker sensor. As described further below, ultrasound imaging device 140 may be positioned in relation to ablation device 130 such that ablation device 130 is at an angle to the ultrasound image plane, thereby enabling the clinician to visualize the spatial relationship of ablation device 130 with the ultrasound image plane and with objects being imaged. Further, the EM tracking system may also track the location of ultrasound imaging device 140. In some embodiments, one or more ultrasound imaging devices 140 may be placed inside the body of the patient. The EM tracking system may then track the location of ultrasound imaging device 140 and ablation device 130 inside the body of the patient. Ultrasound workstation 150 may be used to configure, operate, and view images captured by ultrasound imaging device 140.

Ablation device 130 is used to ablate a lesion or tumor (hereinafter referred to as a "target") by using electromagnetic radiation or microwave energy to heat tissue in order to denature or kill cancerous cells.

The location of ablation device 130 within the body of the patient may be tracked during the surgical procedure. An example method of tracking the location of ablation device 130 is by using the EM tracking system, which tracks the location of ablation device 130 by tracking sensors attached to or incorporated in ablation device 130.

Figure 2:
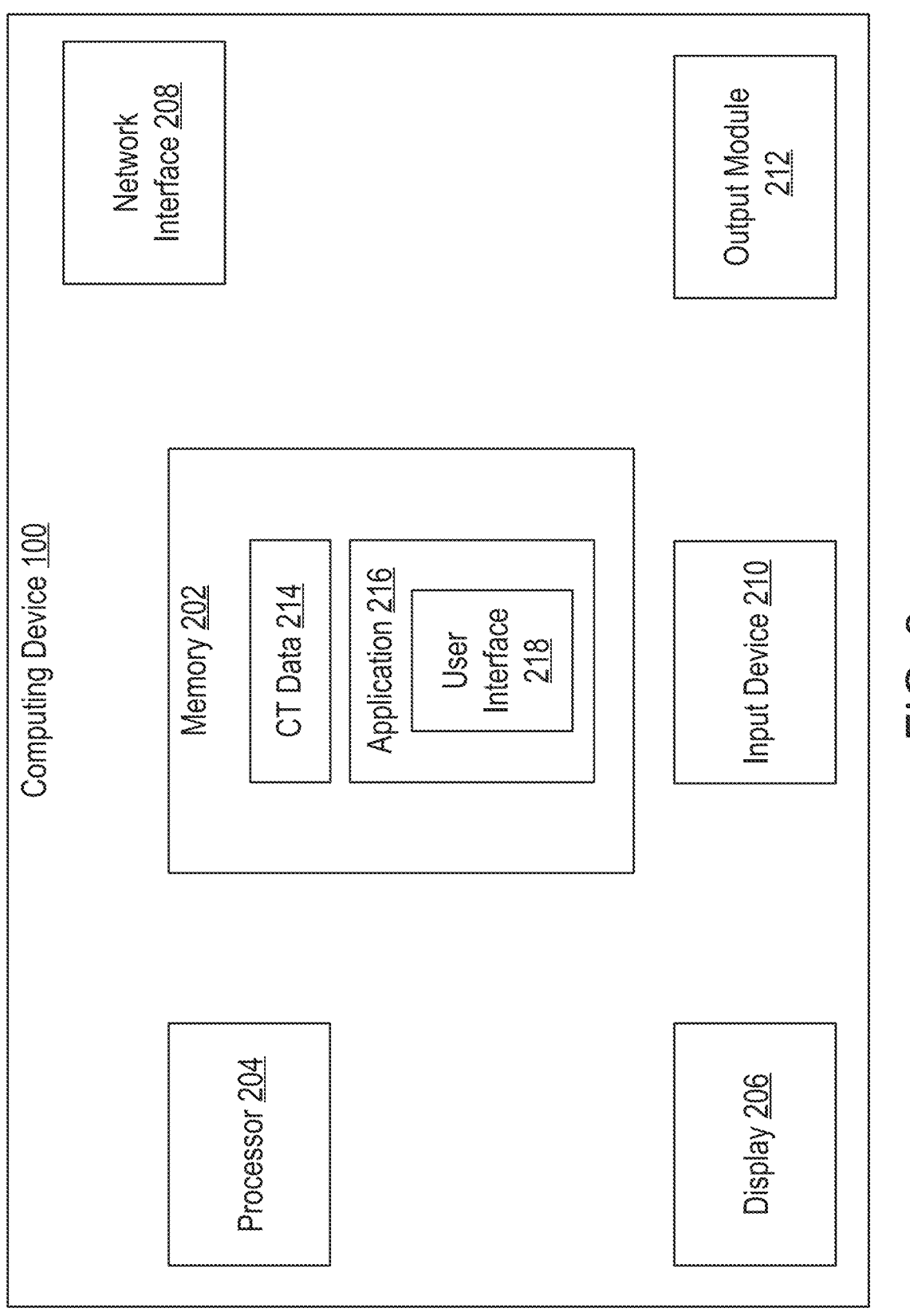
FIG. 2 is a schematic diagram of a computing device which forms part of the microwave ablation procedure system of FIG. 1 in accordance with an aspect of the present disclosure.

FIG. 2 illustrates a system diagram of computing device 100. Computing device 100 may include memory 202, processor 204, display 206, network interface 208, input device 210, and/or output module 212. Memory 202 includes any non-transitory computer-readable storage media for storing data and/or software that is executable by processor 204 and which controls the operation of computing device 100. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules, or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 100.

Memory 202 may store application 216 and/or CT data 214. Application 216 may, when executed by processor 204, cause display 206 to present user interface 218. Processor 204 may be a general-purpose processor, a specialized graphics processing unit (GPU) configured to perform specific graphics processing tasks while freeing up the general-purpose processor to perform other tasks, and/or any number or combination of such processors. Display 206 may be touch sensitive and/or voice activated, enabling display 206 to serve as both an input and output device. Alternatively, a keyboard (not shown), mouse (not shown), or other data input devices may be employed. Network interface 208 may be configured to connect to a network such as a local area network (LAN) consisting of a wired network and/or a wireless network, a wide area network (WAN), a wireless mobile network, a Bluetooth network, and/or the internet. For example, computing device 100 may receive computed tomographic (CT) image data of a patient from a server, for example, a hospital server, internet server, or other similar servers, for use during surgical ablation planning. Patient CT image data may also be provided to computing device 100 via a removable memory 202. Computing device 100 may receive updates to its software, for example, application 216, via network interface 208. Computing device 100 may also display notifications on display 206 that a software update is available.

Input device 210 may be any device by means of which a user may interact with computing device 100, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Application 216 may be one or more software programs stored in memory 202 and executed by processor 204 of computing device 100. As will be described in more detail below, during a planning phase, application 216 guides a clinician through a series of steps to identify a target, size the target, size a treatment zone, and/or determine an access route to the target for later use during the procedure phase. In some embodiments, application 216 is loaded on computing devices in an operating room or other facility where surgical procedures are performed, and is used as a plan or map to guide a clinician performing a surgical procedure, but without any feedback from ablation device 130 used in the procedure to indicate where ablation device 130 is located in relation to the plan. In other embodiments, system 10 provides computing device 100 with data regarding the location of ablation device 130 within the body of the patient, such as by EM tracking, which application 216 may then use to indicate on the plan where ablation device 130 are located.

Application 216 may be installed directly on computing device 100, or may be installed on another computer, for example, a central server, and opened on computing device 100 via network interface 208. Application 216 may run natively on computing device 100, as a web-based application, or any other format known to those skilled in the art. In some embodiments, application 216 will be a single software program having all of the features and functionality described in the present disclosure. In other embodiments, application 216 may be two or more distinct software programs providing various parts of these features and functionality. For example, application 216 may include one software program for use during the planning phase, and a second software program for use during the procedure phase of the microwave ablation treatment. In such instances, the various software programs forming part of application 216 may be enabled to communicate with each other and/or import and export various settings and parameters relating to the microwave ablation treatment and/or the patient to share information. For example, a treatment plan and any of its components generated by one software program during the planning phase may be stored and exported to be used by a second software program during the procedure phase.

Application 216 communicates with a user interface 218 that generates a user interface for presenting visual interactive features to a clinician, for example, on display 206 and for receiving clinician input, for example, via a user input device. For example, user interface 218 may generate a graphical user interface (GUI) and output the GUI to display 206 for viewing by a clinician.

Computing device 100 is linked to display 110, thus enabling computing device 100 to control the output on display 110 along with the output on display 206. Computing device 100 may control display 110 to display output which is the same as or similar to the output displayed on display 206. For example, the output on display 206 may be mirrored on display 100. Alternatively, computing device 100 may control display 110 to display different output from that displayed on display 206. For example, display 110 may be controlled to display guidance images and information during the microwave ablation procedure, while display 206 is controlled to display other output, such as configuration or status information.

As used herein, the term "clinician" refers to any medical professional (i.e., doctor, surgeon, nurse, or the like) or other user of the treatment planning system 10 involved in planning, performing, monitoring, and/or supervising a medical procedure involving the use of the embodiments described herein.

Figure 3:
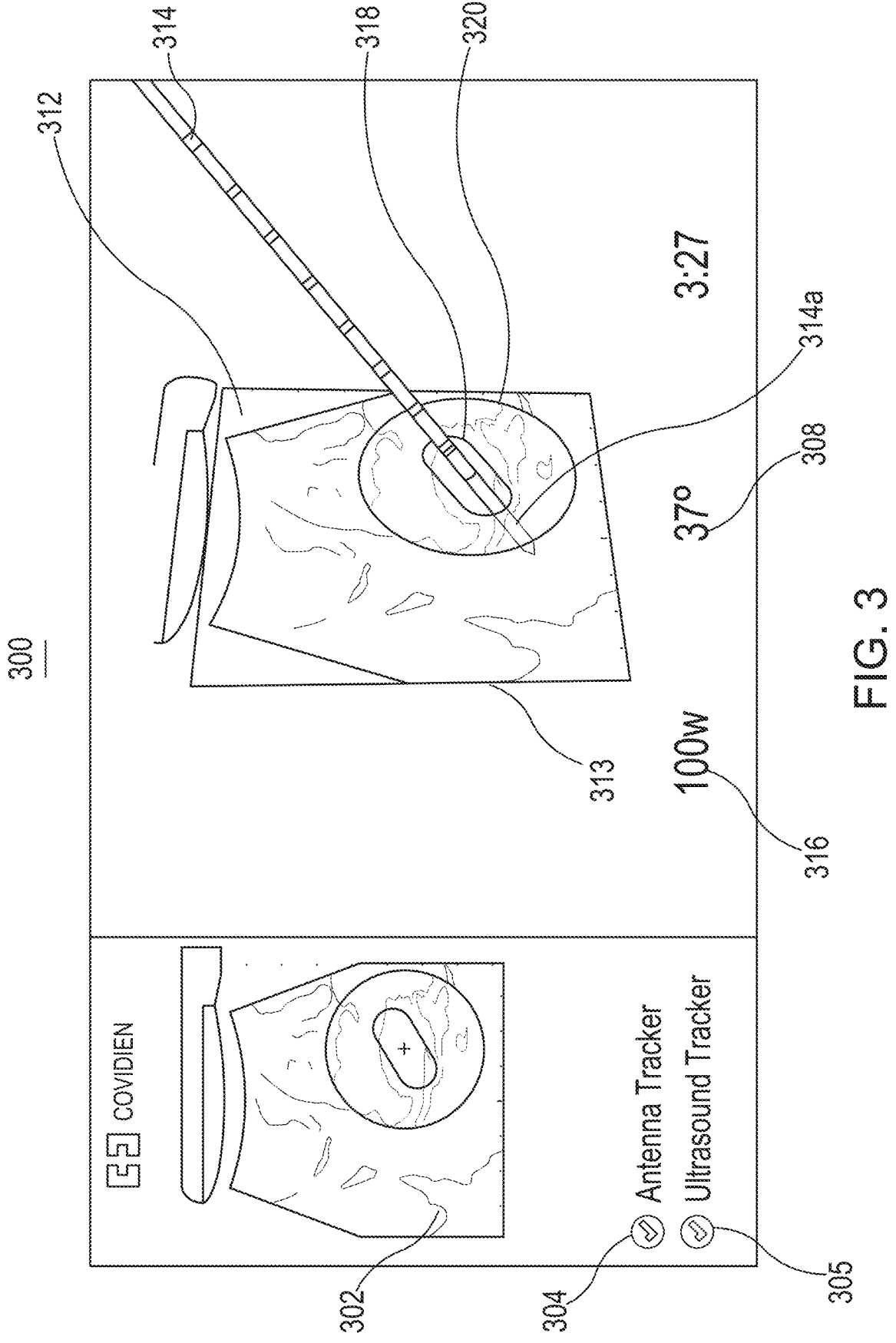
FIG. 3 is an illustration of a user interface including simulated ablation growth displayable on a display of the microwave ablation procedure system of FIG. 1 in accordance with an aspect of the present disclosure.

FIG. 3 illustrates an example user interface 300 displayable on one or both of display 110 and display 206 during an ablation procedure. During an ablation procedure, the clinician navigates ablation device 130 (displayed as ablation device 314 on the user interface 300) along a pathway to the target utilizing the ultrasound imaging system including ultrasound imaging device 140 and ultrasound workstation 150 to visualize placement of the ablation device 130 relative to the target. While ablation device 130 is navigated, application 216 tracks the location of ablation device 130 inside the patient's body and displays the tracked location of ablation device 130 on the user interface. In addition, the application 216 may project a vector displayable on the user interface 300 extending from the end of the ablation device 130 to give an indication to the clinician of the intersecting tissue along the trajectory of the ablation device 130. In this manner, the clinician can alter the approach to a lesion or tumor to optimize the placement with minimum of trauma.

User interface 300 includes a view 302 of the live 2D ultrasound images 313 captured during the procedure. User interface 300 further includes a status indicator 304 for the ablation device 130 and a status indicator 305 for the ultrasound imaging device 140. User interface 300 also includes a view for displaying status messages relating to the ablation procedure, such as a power setting 316 of the ablation device 130, duration of the ablation and/or a time remaining until the ablation procedure is complete, progression of the ablation, and/or temperature feedback 308 from a temperature sensor. User interface 300 also displays the navigation view 312, which includes a representation 314 of ablation device 130 as well as a shadow indicator 314a representing the portion of ablation device 130 which lies below the ultrasound imaging plane, a simulation of ablation growth 318 showing the progression of the ablation zone during application of energy overlayed onto the real time ultrasound images 313 of the surgical site, and a total ablation zone 320 showing the area which will be ablated if the ablation procedure is allowed to run to completion.

Figure 4:
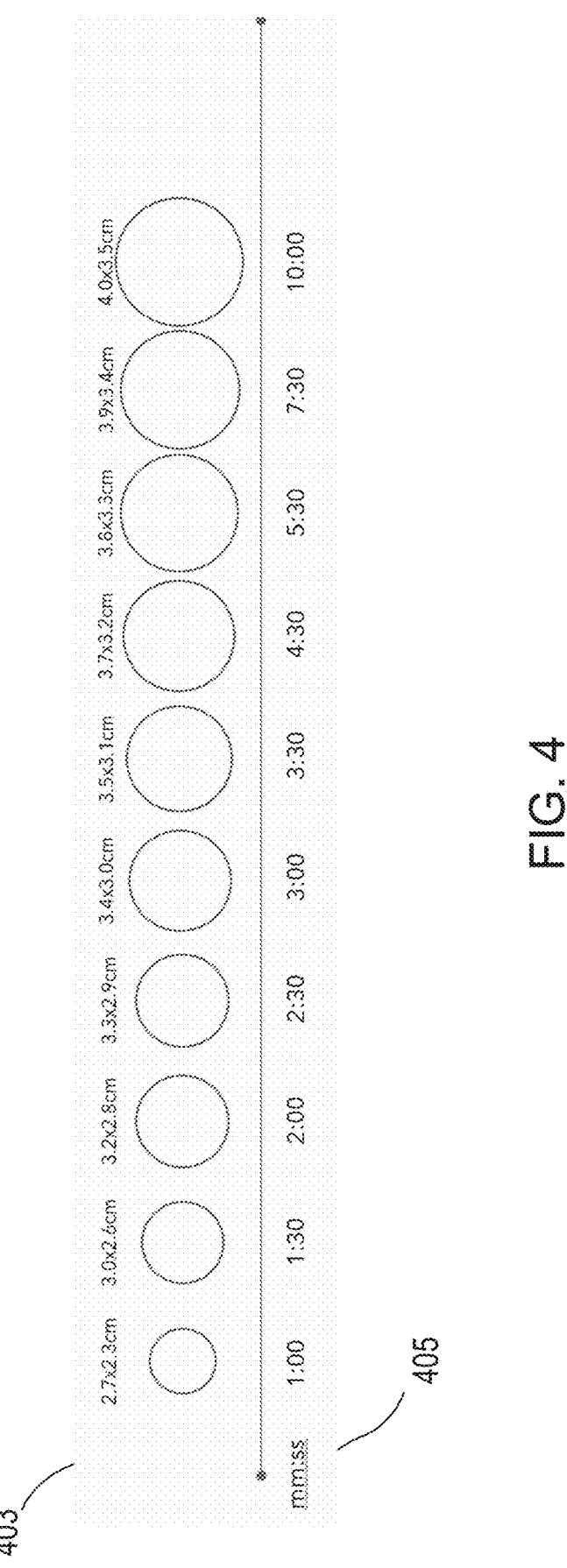
FIG. 4 is an illustration of an ablation zone chart depicting dimensions of simulated ablation growth corresponding to a set power (e.g., 100 W, 45 W) and energy application durations in accordance with an aspect of the disclosure.
Figure 5:
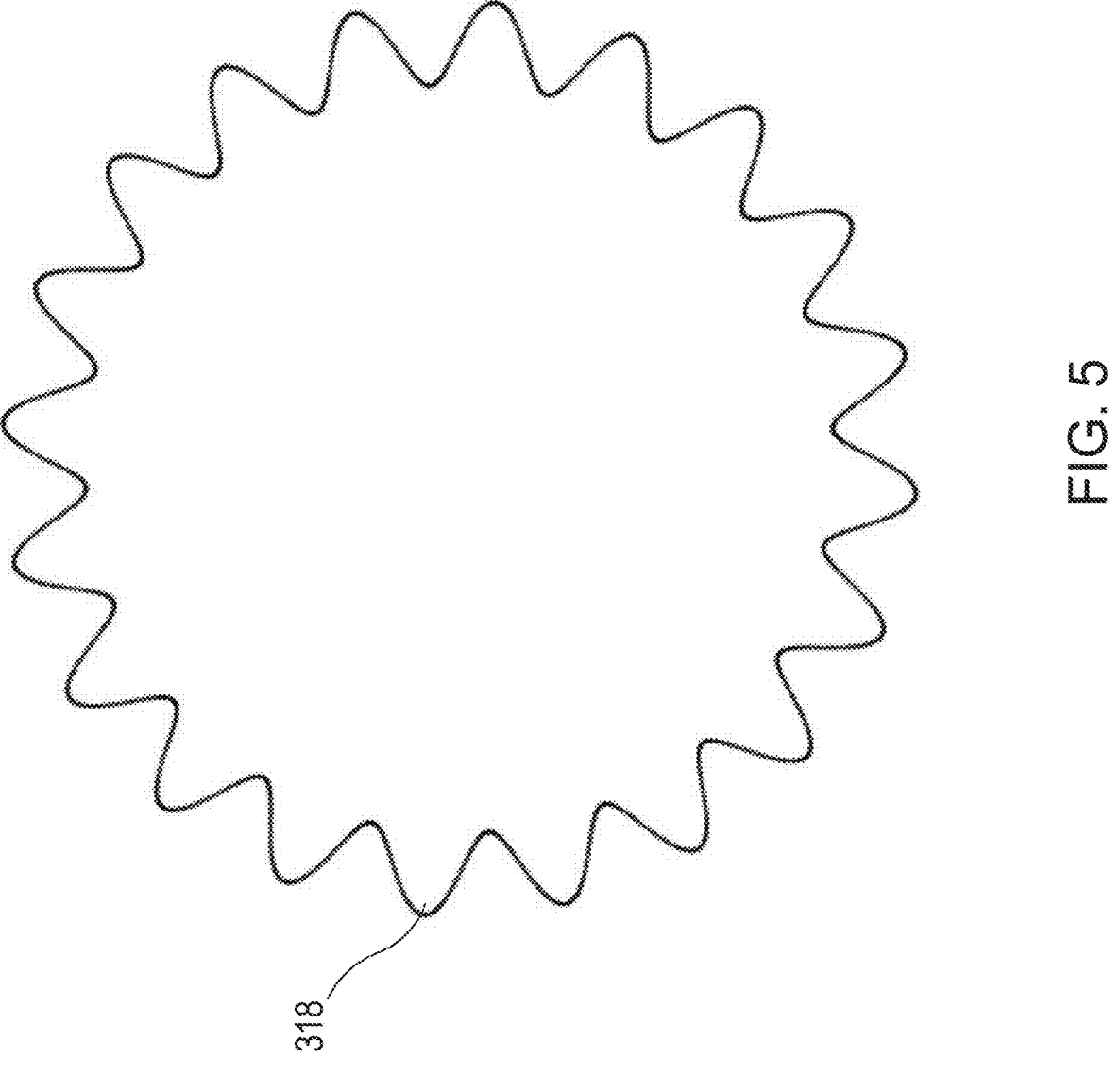
FIG. 5 is an illustration of a simulation of ablation growth including a jagged line outer edge in accordance with an aspect of the disclosure.

Dimensions of the simulation of ablation growth 318 may be based on expected ablation zone sizes at different energy application durations. For example, as illustrated in the ablation zone chart 400 of FIG. 4, dimensions 403 of the ablation zone increase as the energy application duration 405 increases. The data of ablation zone chart 400 may be stored in memory 202 of computing device 100. The simulation of ablation growth 318 may include a solid outer edge which increases in size based on the duration of energy application, a jagged line outer edge which moves and increases in size based on the duration of energy application, and/or a pulsing line outer edge which fades between appearing and disappearing and which increases in size based on the duration of energy application. The appearing and disappearing pulsing line of the simulation of ablation growth 318 prevents the simulation of ablation growth 318 from blocking visibility of objects in the ultrasound images 313.

In aspects, dimensions of the simulation of ablation growth 318 may additionally or alternatively be based on one or more of previously acquired data samples, MRI telemetry data, and/or inferences from contrast enhanced ultrasound Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An ablation system, comprising:

an ablation device configured to ablate a target;

an imaging device configured to capture images of a surgical site in real time, the images of the surgical site including the target and the ablation device positioned relative to the target;

a computing device including:

a memory storing an ablation zone chart having a plurality of simulated ablation growth sizes based on expected ablation zone sizes at different energy application durations, each simulated ablation growth size of the plurality of simulated ablation growth sizes corresponding to an energy application duration and a power setting; and a display configured to display a user interface, the user interface including:

the images of the surgical site in real time;

a simulation of ablation growth overlayed onto the images of the surgical site, wherein a size of the simulation of ablation growth increases with an energy application duration, the size increasing from a first size of the plurality of simulated ablation growth sizes stored on the ablation zone chart to a larger second size of the plurality of simulated ablation growth sizes stored on the ablation zone chart, the first size corresponding to a first energy application duration stored on the ablation zone chart and the second size corresponding to a second energy application duration stored on the ablation zone chart; and a total ablation zone overlay, displayed concurrently with the simulation of ablation growth, the total ablation zone overlay depicting an area expected to be ablated if the ablation procedure is allowed to run to completion at the power setting, wherein the computing device is configured to determine the total ablation zone overlay by selecting, from the ablation zone chart, a simulated ablation growth size that corresponds to an energy application duration that completes the ablation procedure at the power setting.

2. The ablation system of claim 1, wherein the imaging device is an ultrasound imaging device and the images of the surgical site are ultrasound images.

3. The ablation system of claim 1, wherein the simulation of ablation growth includes a solid outer edge.

4. The ablation system of claim 1, wherein the simulation of ablation growth includes a jagged line outer edge.

5. The ablation system of claim 1, wherein the simulation of ablation growth includes a pulsing line outer edge that appears and disappears.

6. The ablation system of claim 1, wherein the expected ablation zone sizes are based on previously acquired data samples.

7. The ablation system of claim 1, wherein the expected ablation zone sizes are based on MRI telemetry data.

8. The ablation system of claim 1, wherein the expected ablation zone sizes are based on inferences from contrast enhanced ultrasound.

9. An ablation system, comprising:

a computing device including:

a display; and a memory storing an ablation zone chart having a plurality of simulated ablation growth sizes based on expected ablation zone sizes at different energy application durations each simulated ablation growth size of the plurality of simulated ablation growth sizes corresponding to an energy application duration and a power setting, wherein the computing device is configured to:

receive images of a surgical site in real time, the images of the surgical site including a target and an ablation device positioned relative to the target;

display the received images on the display;

overlay a simulation of ablation growth onto the displayed images of the surgical site, wherein a size of the simulation of ablation growth increases with an energy application duration, the size increasing from a first size of the plurality of simulated ablation growth sizes stored on the ablation zone chart to a larger second size of the plurality of simulated ablation growth sizes stored on the ablation zone chart, the first size corresponding to a first energy application duration stored on the ablation zone chart and the second size corresponding to a second energy application duration stored on the ablation zone chart; and overlay a total ablation zone onto the displayed images of the surgical site concurrently with the simulation of ablation growth, the total ablation zone overlay depicting an area expected to be ablated if the ablation procedure is allowed to run to completion at the power setting, wherein the computing device is configured to determine the total ablation zone overlay by selecting, from the ablation zone chart, a simulated ablation growth size that corresponds to an energy application duration that completes the ablation procedure at the power setting.

10. The ablation system of claim 9, further comprising an ultrasound imaging device configured to capture the images of the surgical site.

11. The ablation system of claim 9, wherein the simulation of ablation growth includes a solid outer edge.

12. The ablation system of claim 9, wherein the simulation of ablation growth includes a jagged line outer edge.

13. The ablation system of claim 9, wherein the simulation of ablation growth includes a pulsing line outer edge that appears and disappears.

14. The ablation system of claim 9, wherein the expected ablation zone sizes are based on previously acquired data samples.

15. The ablation system of claim 9, wherein the expected ablation zone sizes are based on MRI telemetry data.

16. The ablation system of claim 9, wherein the expected ablation zone sizes are based on inferences from contrast enhanced ultrasound.

17. A user interface displayable on a display of an ablation system, the user interface comprising:

real time images of a surgical site, the real time images of the surgical site including a target and an ablation device positioned relative to the target, wherein the real time images of the surgical site are stored on a memory of the ablation system, the memory storing an ablation zone chart having a plurality of simulated ablation growth sizes based on expected ablation zone sizes at different energy application durations, each simulated ablation growth size of the plurality of simulated ablation growth sizes corresponding to an energy application duration and a power setting;

a simulation of ablation growth overlayed onto the real time images of the surgical site, wherein a size of the simulation of ablation growth increases with an energy application duration, the size increasing from a first size of the plurality of simulated ablation growth sizes stored on the ablation zone chart to a larger second size of the plurality of simulated ablation growth sizes stored on the ablation zone chart, the first size corresponding to a first energy application duration stored on the ablation zone chart and the second size corresponding to a second energy application duration stored on the ablation zone chart; and a total ablation zone overlay, displayed concurrently with the simulation of ablation growth, the total ablation zone overlay depicting an area expected to be ablated if the ablation procedure is allowed to run to completion at the power setting, wherein the total ablation zone overlay is determined based on a simulated ablation growth size from the ablation zone chart that corresponds to an energy application duration that completes the ablation procedure at the power setting.

18. The user interface of claim 17, wherein the simulation of ablation growth includes at least one of a solid outer edge, a jagged line outer edge, or a pulsing line outer edge that appears and disappears.

19. The user interface of claim 17, wherein the expected ablation zone sizes are based on previously acquired data samples.

20. The user interface of claim 17, wherein the expected ablation zone sizes are based on at least one of MRI telemetry data or inferences from contrast enhanced ultrasound.

* * * * *